United States Patent
Duncan et al.

(10) Patent No.: US 9,588,092 B2
(45) Date of Patent: Mar. 7, 2017

(54) RELATIVE HUMIDITY SATURATED SALT GENERATOR

(71) Applicant: Wagner Electronic Products, Inc., Rogue River, OR (US)

(72) Inventors: Timothy Duncan, Grants Pass, OR (US); Edward D. Wagner, Rogue River, OR (US); Eric Wagner, Grants Pass, OR (US)

(73) Assignee: Wagner Electronic Products, Inc., Rogue River, OR (US)

( * ) Notice: Subject to any disclaimer, the term of this patent is extended or adjusted under 35 U.S.C. 154(b) by 193 days.

(21) Appl. No.: 14/612,441

(22) Filed: Feb. 3, 2015

(65) Prior Publication Data

US 2016/0123940 A1    May 5, 2016

Related U.S. Application Data

(60) Provisional application No. 62/084,390, filed on Nov. 25, 2014, provisional application No. 62/074,326, filed on Nov. 3, 2014.

(51) Int. Cl.
   *G01N 33/00* (2006.01)
   *G01N 25/56* (2006.01)

(52) U.S. Cl.
   CPC ......... *G01N 33/0006* (2013.01); *G01N 25/56* (2013.01)

(58) Field of Classification Search
   CPC ............ G01N 33/0006; G01N 27/121; G01N 27/225; G01N 27/4163; G01N 25/56; B01D 53/228; B01D 2053/221
   See application file for complete search history.

(56) References Cited

U.S. PATENT DOCUMENTS

| 3,665,748 A | * | 5/1972 | Mator ................ G01N 33/0006 |
| | | | 261/94 |
| 3,832,882 A | * | 9/1974 | Schoen, Jr. ............ G01W 1/18 |
| | | | 73/1.03 |
| 4,269,057 A | * | 5/1981 | Ong .................... G01N 33/0006 |
| | | | 422/83 |
| 4,385,910 A | * | 5/1983 | Eilers ................. G01N 33/0006 |
| | | | 73/1.04 |
| 4,742,708 A | * | 5/1988 | Porter ................ G01N 33/0006 |
| | | | 73/1.04 |

(Continued)

*Primary Examiner* — Peter Macchiarolo
*Assistant Examiner* — Natalie Huls
(74) *Attorney, Agent, or Firm* — Klarquist Sparkman, LLP

(57) ABSTRACT

Disclosed RH generators include a lower component having a first chamber and an upper component including a second chamber, the upper component being coupled to the lower component to couple the first chamber to the second chamber. The first chamber is configured to contain liquid water and generate 100% RH, while the second chamber is configured to contain salt and generate a second RH less than 100% RH. A first membrane is positioned between the first chamber and the second chamber to allow water vapor to pass between the first and second chambers while blocking liquid water, the salt, and other larger molecules. The upper component is couplable to an RH probe with a second membrane separating the second chamber from the RH probe, which allows water vapor to pass between the second chamber and the RH probe to expose the RH probe to the second RH.

20 Claims, 7 Drawing Sheets

(56) References Cited

U.S. PATENT DOCUMENTS

| | | | | |
|---|---|---|---|---|
| 4,998,431 A | * | 3/1991 | Jappinen | G01N 33/0006 239/34 |
| 5,086,642 A | * | 2/1992 | Jessel | B01L 3/508 422/939 |
| 5,293,770 A | * | 3/1994 | Hansen | G01N 27/4163 204/401 |
| 6,039,696 A | * | 3/2000 | Bell | A61M 16/08 128/204.21 |
| 2005/0121338 A1 | * | 6/2005 | Inoue | C12P 13/02 205/775 |
| 2011/0277547 A1 | * | 11/2011 | Duncan | G01N 27/048 73/335.02 |
| 2014/0311214 A1 | * | 10/2014 | Wolf, Jr. | G01N 33/0006 73/23.3 |
| 2015/0160190 A1 | * | 6/2015 | Ravishankar | G01N 33/0006 73/1.06 |

* cited by examiner

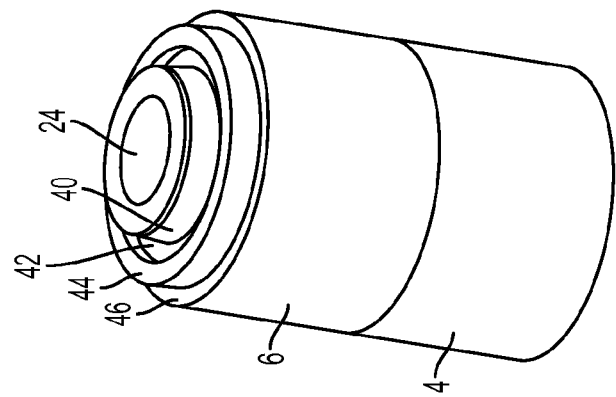
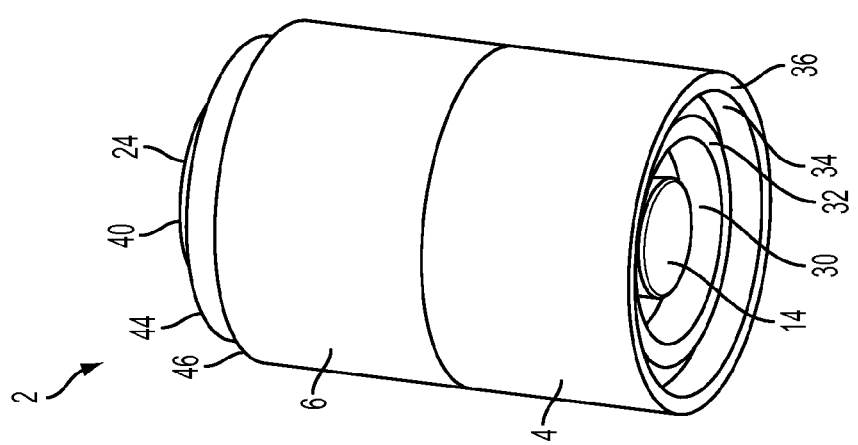

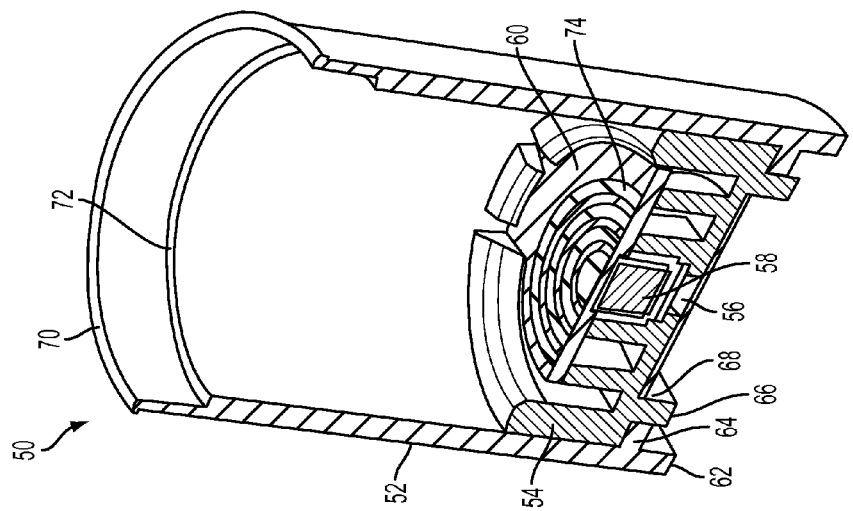
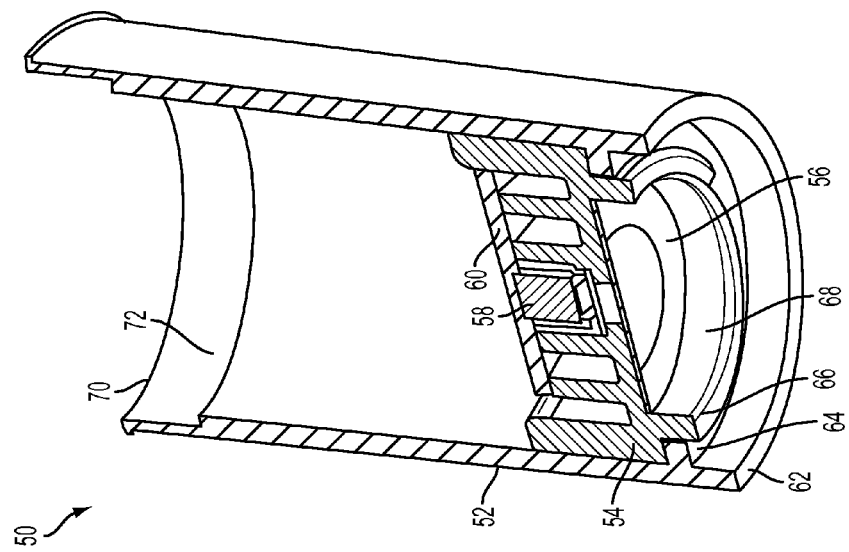

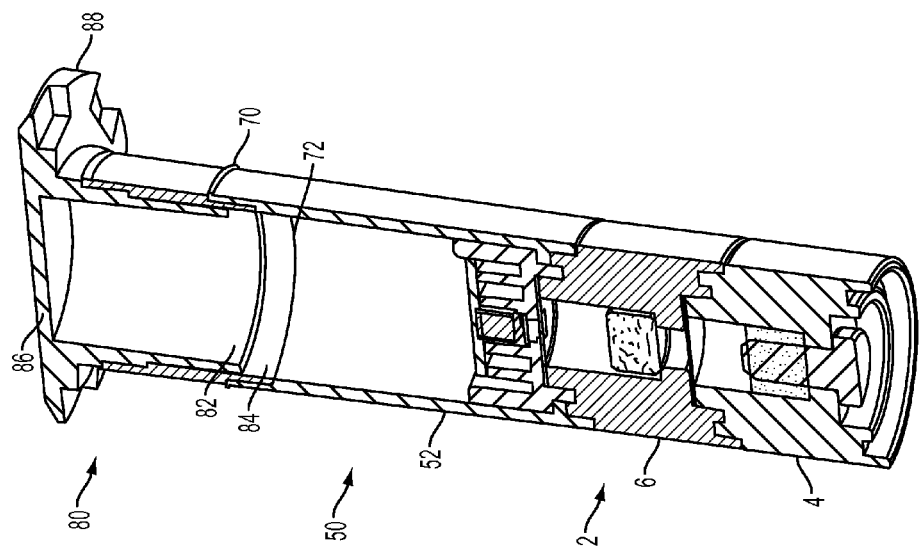
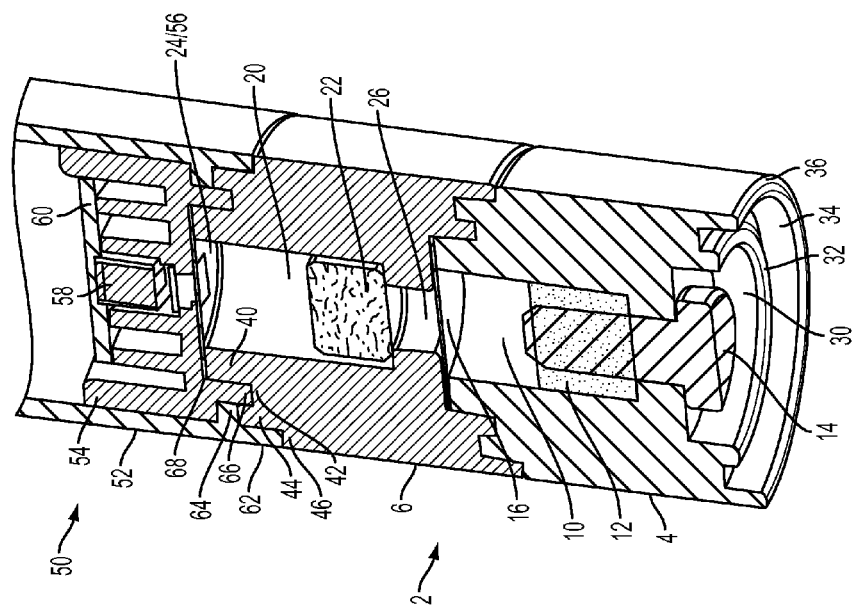

RELATIVE HUMIDITY SATURATED SALT GENERATOR

CROSS-REFERENCE TO RELATED APPLICATIONS

This application claims the benefit of U.S. Provisional Application No. 62/074,326 filed on Nov. 3, 2014, and claims the benefit of U.S. Provisional Application No. 62/084,390 filed on Nov. 25, 2014, both of which are incorporated by reference herein in their entirety.

FIELD

This application is related to devices and methods for generating a known relative humidity.

BACKGROUND

Digital relativity humidity (RH) sensors can be calibrated by exposing the RH sensor to known RH and temperature environments. An RH sensor can be initially calibrated during manufacturing and re-calibrated periodically during normal use. A common calibration method is to use saturated salt solutions as defined in ASTM E-102, which specifies mixing specific salts with distilled or "pure" water. Saturated salts of specific salts will produce an equilibrium air environment above the saturated salt with a known % RH level, which can then be used to calibrate an RH sensor.

A saturated salt solution within an enclosed volume will create a standard constant relative humidity in the head space above the surface of the saturated salt solution. ASTM E-104 provides procedures for creating saturated salt solutions and a table of reference values for RH values which differ depending on the salt used and the temperature of the solution. These salt solutions are used to create known RH levels for validating the accuracy of an RH probe's integrated RH sensor. However, known devices that utilize such a saturated salt solution all require distilled or pure water.

SUMMARY

Described herein are devices and systems that generate an air environment with a known level of relative humidity (% RH). Disclosed embodiments use a specific salt, such as sodium bromide, sodium chloride, or potassium chloride, with water to produce a saturated salt within an enclosed environment. One aspect of the disclosed technology is that the devices can use ordinary potable water/tap water instead of the conventionally required distilled water. Disclosed devices are able to utilize ordinary tap water by first creating a pure water vapor from the ordinary tap water. Vapor from a lower reservoir of ordinary tap water is allowed to pass through a semi-permeable membrane via diffusion due to the gradient pressure difference with the upper chamber that encloses the salt, which has a lower than 100% RH air environment. The salt then captures the pure water vapor via the vapor pressure differences around the salt and the air and generates an equilibrated air environment around the salt with a known % RH that is determined by the specific salt used. This can then be used as a specific % RH generator by allowing that air to pass out the top through another semi-permeable membrane, which can be used to expose an RH sensor to the know RH % and test the RH sensor's accuracy. The semi-permeable membranes, which can be made from PTFE filter material for example, can have a pore size sufficient to allow water vapor molecules to pass through, but block larger molecules that may otherwise be detrimental to an RH sensor.

Disclosed devices can act as a molecular pump to pump water from a "liquid isolated" first chamber to a second chamber that contains salt. The pump acts by transferring water molecules that vaporize from the water reservoir through a semi-permeable membrane to the second chamber, where they are then captured and condensed onto the salt in the second chamber. As long as the salt is not fully saturated by the condensing water, an RH level lower than the 100% RH produced by the first chamber will remain and continue to "pump" water vapor from the first chamber, until all the water has been transferred to the second chamber, which will result in both chambers having an environment with the equilibrated % RH as determined by the specific salt used. Since the second chamber is "filled" via water vapor through the membrane, ordinary potable/tap water can be used as the result is pure water in the second chamber, via the vaporization, filtering, and subsequent condensation of pure water vapors into the second chamber.

The foregoing and other objects, features, and advantages of the disclosed technology will become more apparent from the following detailed description, which proceeds with reference to the accompanying figures.

BRIEF DESCRIPTION OF THE DRAWINGS

FIG. 1A shows water in a lower chamber that is filled through a rubber plug. FIG. 1B shows migration of the water through evaporation to an upper chamber in the upper component. A filter allows water to pass from the lower chamber to the upper chamber. A second membrane at a top end of the upper chamber allows exposure of an RH sensor of an RH probe to the equilibrated RH level. The upper and lower components can be integrated or connected together with an air-tight fit.

FIGS. 2A and 2B are perspective views of the upper and lower components of FIGS. 1A and 1B. An annular rim at the top of the upper component allows connection to an RH probe body with an airtight fit.

FIGS. 3A and 3B are cross-sectional perspective views of an RH probe with a RH sensor circuit board at the lower end thereof. The bottom of the RH probe body can receive the annular rim of the upper component shown in FIG. 2B with an airtight fit so that the upper and lower components can be coupled and decoupled from the RH probe body.

FIGS. 5A and 5B are cross-sectional perspective views of an assembly including the upper and lower components attached to an RH probe with an air-tight fit. The outer walls of the RH probe can align with the outer walls of the components containing the upper and lower chambers so as to appear as a unitary body.

DETAILED DESCRIPTION

Figure 1B:
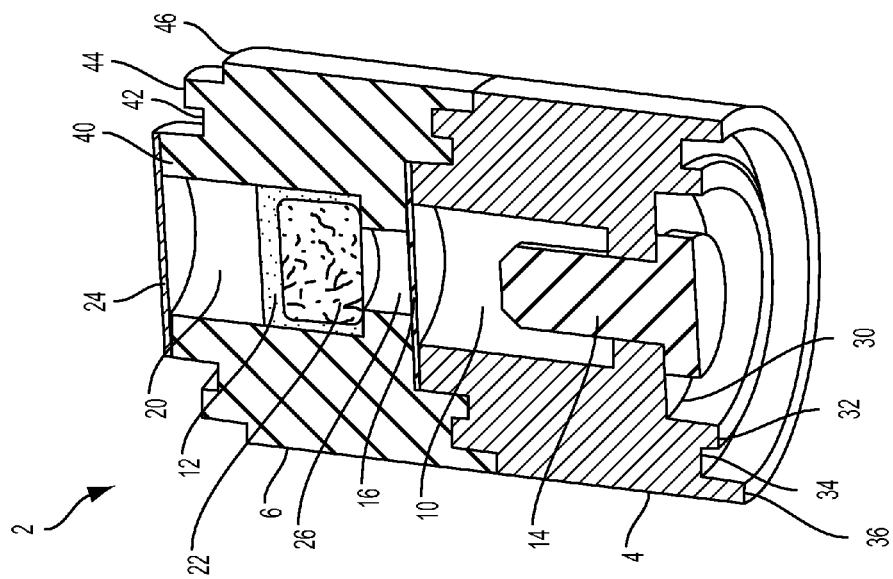
FIGS. 1A and 1B are cross-sectional perspective views of an examplary RH generator including an upper component and a lower component.
Figure 1A:
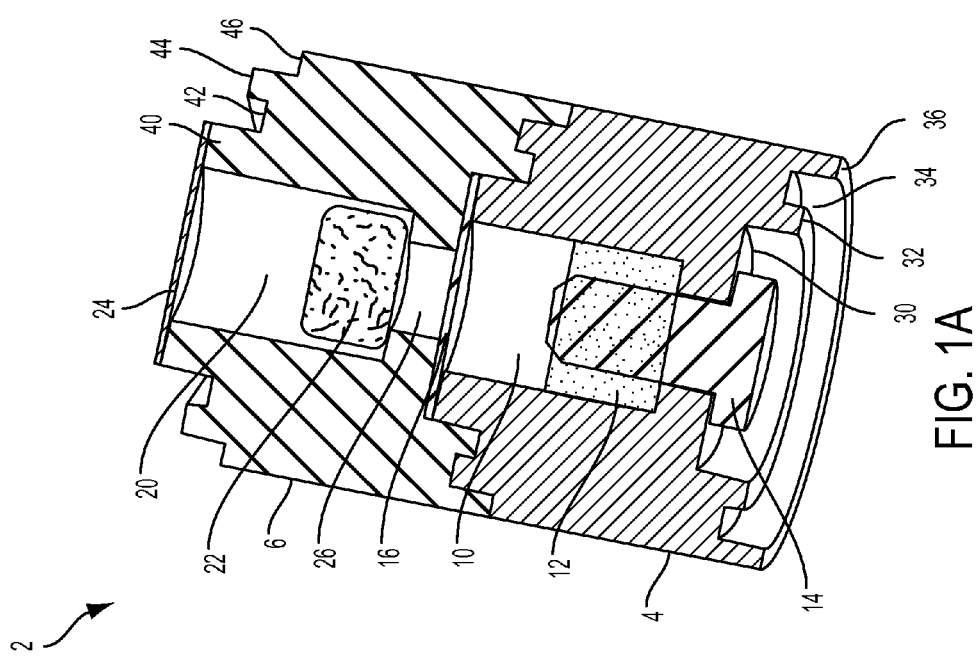
Figure 4B:
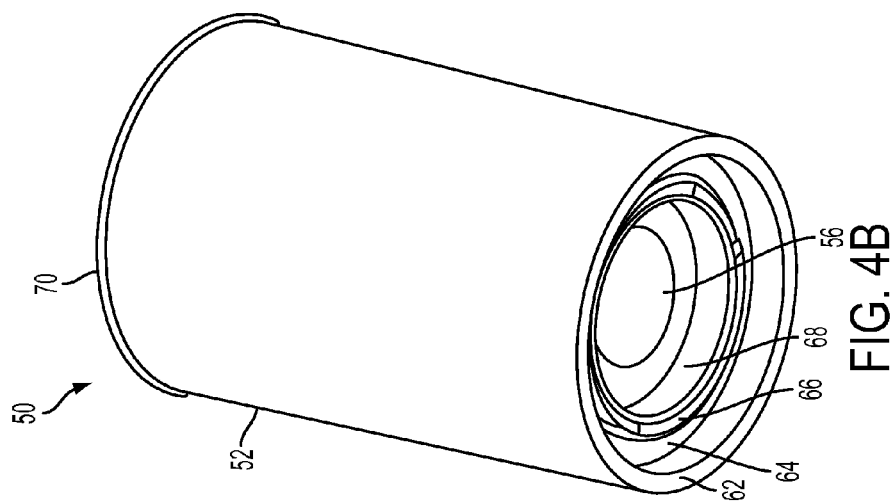
FIG. 4B is a perspective view of the RH probe showing the membrane inserted in the bottom of the RH probe body, instead of being attached to the upper chamber, as is shown in FIG. 2B.
Figure 4A:
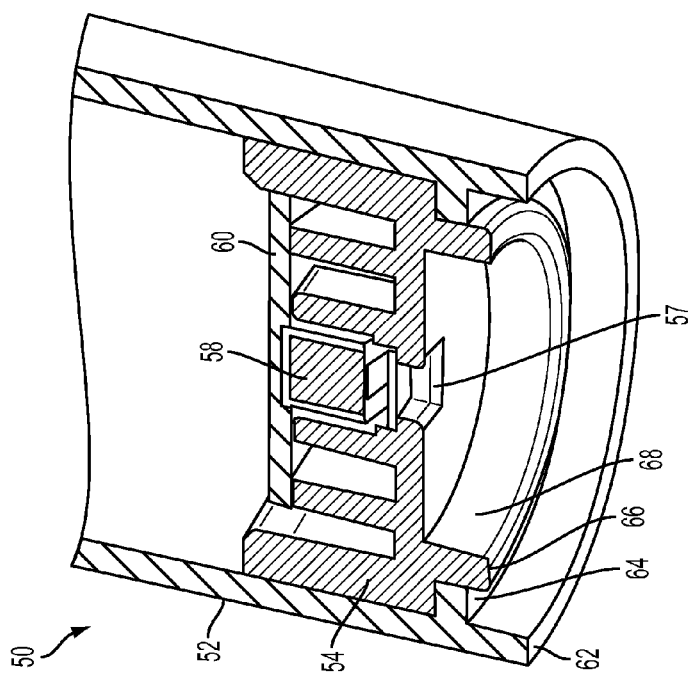
FIG. 4A is a cross-sectional perspective view of the RH probe body with a lower membrane removed.

FIGS. 1A, 1B, 2A, and 2B show an exemplary embodiment of a relative humidity (RH) generator device 2 that can be used to calibrate an RH sensor. The illustrated device 2 includes two main components: a first, or lower, component 4 and a second, or upper, component 6. The lower component 4 includes a lower chamber 10 adapted to contain a volume of ordinary tap water 12 and the upper component 6 includes an upper chamber 20 adapted to contain a salt 22.

The components 4 and 6 can be made of a rigid material that has a very low water vapor permeation constant and very low maximum water absorption constant, such as acrylic. It can also be desirable for the components 4 and/or 6 to be made from material that results in transparency of the components so that a user can visually see the amount and position of the water and salt inside the device.

The lower chamber 10 has a lower opening that is sealed with a plug 14 and an upper opening that is covered by a first membrane 16, which separates the lower chamber from the upper chamber. The upper chamber 20 includes an upper opening that is covered by another membrane 24. The membranes 16 and 24 can comprise PTFE and/or other suitable filter materials that allow molecular water vapor transport between the chambers but blocks the transport of liquid water or larger molecules, such as VOCs.

A suitable amount of salt 22 is placed inside the upper chamber 20 such that if the upper chamber is filled additionally with water, the water would be overly saturated with the salt, i.e. the molarity would be such that it would greater than what the amount of water could absorb. The salt 22 can be in a solid block form and/or in a powder form. The lower chamber 10 is filled partially with ordinary tap water 12 and sealed within by the plug 14 (e.g., a removable rubber plug), which is inserted into the bottom of the lower chamber 10. At any time, more water can be added by removing the plug 14, adding water into the lower chamber 10, and then reinserting the plug.

In an exemplary method of assembling the device 2, the membrane 16 can placed on the bottom of the upper component 6 covering the lower opening of the chamber 20, or the membrane 16 can be placed on the top of the lower component 4 covering the upper opening of the chamber 10. The lower component 4 can then be attached to the upper component 6 such that a water-tight seal is formed between the two components 4, 6 and the membrane 16 is secured between and fully separates the two chambers 10, 12. The two components 4, 6 can be secured together in a releasable manner and/or can be secured together in a semi-permanent manner, such as using a compression fit, friction fit, snap fit, a threaded attachment, a weld, an adhesive, etc. In some embodiments, the two components can be detached and reattached to each other, such as to access the membrane 16. In some embodiments, the securement between the components is semi-permanent and under normal use, during its lifetime, there is no need to unassemble the two main components 4, 6.

In some embodiments, such the illustrated embodiment, the upper end of the lower component 4 can include projections and recesses that correspond to other projections and recesses on the lower end of the upper component 6. In some embodiments, concentric annular ridges and grooves can be provided. For example, as shown in FIGS. 1A, 1B, 2A, and 2B, the lower ends of the components 4, 6 can include a lower inner recess 30, lower inner rim 32, lower outer recess 34, and lower outer rim 36, and the upper ends of the components can include an upper inner rim 40, upper inner recess 42, upper outer rim 44, and upper outer recess 46. The upper features can mate frictionally with the lower features to secure the two components 4, 6 together. For example, the upper inner rim 40 fits into the lower inner recess 30, the lower inner rim 32 fits into the upper inner recess 42, the upper outer rim 44 fits into the lower outer recess 34, and the lower outer rim 36 fits into the upper outer recess 46. The fit between the opposing projections and recesses can be friction fits, for example, to hold the two components together and provide water-tight sealing. In some embodiments, the lower component 4 and the upper component 6 can be substantially similar or identical in structure. In some embodiments, the components 4 and 6 can be swapped and they can be secured together with either on top serving as the salt-containing component and the other on the bottom serving as the water origination component.

Once the lower opening of the upper chamber 20 is covered by the membrane 16 (either before or after the lower component 4 is attached to the upper component 6), an appropriate amount of salt 22 can be placed in the upper chamber 20. The salt 22 can completely or partially cover the lower opening of the upper chamber 20, so long as water vapor from passing up through the membrane 16 can permeate and pass through the salt to create the desired RH environment above the salt in the chamber 20.

In some embodiments, the lower component 4 and the upper component 6 can be a single component and/or can be manufactured together and be inseparable. In such embodiment, the membrane 16 can be inserted from the top or bottom and positioned between the upper and lower chambers prior to adding the salt into the top chamber from the top and adding the water into the lower chamber from the bottom and sealing the bottom chamber with a plug and optionally sealing the top chamber with the upper membrane 24.

After the salt 22 is placed in the upper chamber 20, the upper membrane 24 can be placed on the top of the upper component 6 to close off the upper chamber. In some embodiments, the upper opening of the upper chamber is left open after the salt is added, and the upper membrane 24 is included as part of an RH probe such that when the RH probe is pressed against the top of the upper component 6, the membrane 24 covers the upper opening of the upper chamber 20.

Any kind of water 12 can be added to the lower chamber 10, then the plug 14 is inserted into the bottom opening of the lower chamber, sealing in the liquid water. In some embodiments, no plug is included in the lower component. In such embodiments, water can be added into the lower chamber 10 through its upper opening when the lower and upper components 4, 6 are not attached and when the membrane 16 is not covering the lower chamber. The water 12 can be ordinary tap water, other types of undistilled water, distilled water, or other kinds of water. There is no need to use distilled or purified water since the device 2 inherently distils or purifies the water.

In use, 100% RH is generated in the air in the lower chamber 10 from the liquid water 10. Any amount of water can be added to and sealed within the lower chamber to generate the 100% RH, though a small amount of water will be depleted sooner than a larger amount of water during use. The 100% RH is then used as a source to saturate the salt 22 that will then produce a known constant RH below 100% in the air in the upper chamber 20. In the lower chamber 10, 100% RH is naturally generated in the air in the head space above the water 12. The water vapor slowly diffuses through the membrane 16. Once that water vapor enters the upper chamber 20 and encounters the salt 22, part of the water vapor is adsorbed and eventually absorbed as the salt becomes wetter and more saturated. Inside the upper chamber 20, the air above the salt equilibrates to a known RH level below 100% that is based on the particular salt used and the temperature. Equilibrium RH is achieved in the upper chamber 20 above the salt 22 in the head space and continues to maintain at that equilibrium. As more water vapor is diffused through the membrane 16 to the upper chamber the saturated salt adsorbs/absorbs the excess moisture that would otherwise upset the equilibrium RH. This process continues until all the water in the lower chamber has been transferred to the upper chamber, at which time the lower chamber will also reach an equilibrium with the upper chamber's RH level and both chambers will be at the RH dictated by the specific saturated salt solution. The water vapor that is produced by the lower chamber and diffused through the membrane 16 to the upper chamber is of a "pure" nature like what is produced by a normal distillation process.

The entire device 2 can be thought of as employing a two-stage filtration process whereby a 100% humidity air environment reservoir is generated by the first stage, which is transferred to the second stage where that humidity is brought into a lower relative humidity equilibrium due to the presence of a particular salt, the particular salt dictating what that lower RH value is. The lower RH valued generated air environment is then allowed to pass out through the upper membrane 24 to be used for testing a RH sensor for accuracy by comparing the RH sensor readout to the known RH level produced by the RH generator device 2. When the part that is exposed to the RH sensor is in a somewhat airtight enclosure with the sensor, equilibrium RH can be achieved quickly as long as that enclosed volume is relatively small. Once the water in the lower reservoir 12 has diffused through to the upper chamber 10, the upper chamber will maintain the equilibrium RH value until all the water vapor has escaped through exposure and testing of RH sensors. When the water level is low, the lower chamber 10 can be re-filled with regular water to "recharge" the device 2.

The transfer mechanism that transports the water from the lower to the upper chamber is achieved through partial pressure gradient of the water vapor. The high 100% RH in the lower chamber and the equilibrated lower RH level of the upper chamber (due to the presence of the salt material and ambient air) creates a pressure gradient that drives the diffusion of the water vapor from the higher concentration in the lower chamber through the membrane 16 to the lower pressure in the upper chamber. The wetted/saturated salt ensures that this pressure gradient remains in effect.

The disclosed RH generation devices can be used with RH probes by coupling the bottom of the RH probe to the top of the upper component 6 with an air-tight fit. An RH sensor in the probe can therefore be exposed to the equilibrated RH level in the upper chamber 20 through the upper filter 24.

Figure 6:
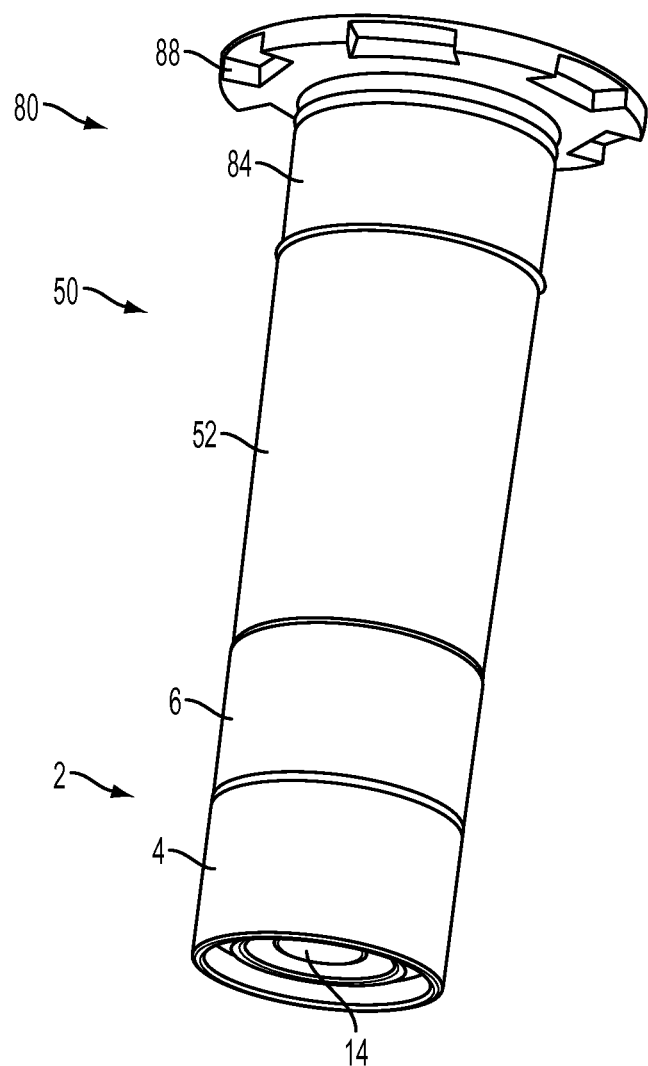
FIG. 6 shows a perspective view of the assembly of FIG. 5B.

FIGS. 3A, 3B, 4A, and 4B illustrated an exemplary RH probe 50 that includes an RH sensor 58 that can be calibrated by using the disclosed RH generation devices. FIGS. 5A, 5B, and 6 show the RH generator device 2 coupled to the RH probe 50. The probe 50 can include a rigid, generally cylindrical body 52, an inner mount 54, an integrated circuit 60, the RH sensor 58, and optionally a lower filter 56 that replaces or works together with the filter 24 of the device 2. The body 52 and/or the inner mount 54 can include a lower outer rim 62, lower outer recess 64, lower inner rim 66, and lower inner recess 68, which can be sized and shaped similarly to the lower features 30, 32, 34, 36 of the device 2 to enable the lower end of the probe 50 to be attached to the upper end of the upper component 6 during testing of the RH sensor 58, as shown in FIG. 5A.

The lower inner recess 68 of the probe 50 can receive the filter 56 in some embodiments. The mount 54 can include an opening to expose the RH sensor 58 to the controlled RH environment created by the upper chamber 20. When the probe 50 is not coupled to the RH generator device 2, the lower end of the probe can be covered with a protective cap. Similarly, when not in use, the upper end of the device 2 can be covered with a protective cap that prevents water vapor from exiting the upper chamber through the filter 24 or through an uncovered upper opening.

The body 52 can have an open upper end 70 that is configured to receive a reader module (not shown) that is inserted into the probe 50 into contact with electrical connector pads 74 on the upper surface of the IC 60 to read RH measurement data obtained from the RH sensor 58.

As shown in FIG. 5B and in FIG. 6, the probe 50 can also receive a cap 80 that covers the open upper end 70 of the body 52 when a reader module is not inserted into the probe. The cap 80 can include a lower part 84 that slides inside the body 52 to an inner ledge 72, and the cap can include an upper part 82 that joins with the lower part and includes a closed upper end 86 and an outer rim 88.

After being calibrated with the RH generator device 2, the RH probe 50, or other types of RH probes compatible with the RH generator device 2, can be inserted into concrete or other environments where it is desired to measure or monitor the RH levels periodically. More information regarding RH sensors, RH probes, RH reader modules, and associated methods can be found in U.S. Patent Publication 2011/0277547, published on Nov. 17, 2011, from U.S. patent application Ser. No. 13/104,666, filed May 10, 2011, which is incorporated by reference herein in its entirety.

In alternative embodiments, an RH generator device can be configured to include two or more different salts and can therefore generator two or more corresponding predetermined RH levels. In some embodiments, the upper component 6 can be configured with two or more isolated upper chambers, each containing a different salt. The device 2 can be adjustable such that a selected one of the upper chambers can be positioned into communication with the lower chamber and used to test an RH sensor. For example, the upper component can be rotatable relative to the lower component about a vertical central axis. At one rotational position, a first upper chamber is in vapor communication with the lower chamber while a second upper chamber is closed off and not in vapor communication with the lower chamber. In this first position, water vapor from the lower chamber passes through a membrane into the first upper chamber and produces a first predetermined RH level in the first upper chamber based on a first salt positioned therein. The upper chamber can then be rotated to close off the first upper chamber from the lower chamber and place the second upper chamber in vapor communication with the lower chamber, such that water vapor from the lower chamber passes through a membrane (the same one or a different one) into the second upper chamber and produces a second predetermined RH level in the second upper chamber based on a second salt positioned therein. Each upper chamber can have its own respective upper opening that may or may not be covered with an upper membrane. The interface between the upper component and the lower component can be configured to facilitate rotating the two components relative to each other to the different available rotational positions. For example, markings can be provided on the outer surface that indicate the different available position, gripping features can be provided on the outer surfaces, biasing features can be provided in the interface to bias the two components into the desired positions and provide tactile feedback to the user, and/or other features can be provided to facilitate the user adjusting the device to use the different upper chambers.

In some embodiments, a kit or set including a plurality of different upper components can be provided with and alternatively used with the same lower component, with each upper component containing a different salt and configured to produce a different RH %. The upper components can readily detach and reattach to the lower component. Each component can be fully sealed, even if a double membrane is provided between them when they are attached together.

Figure 7:
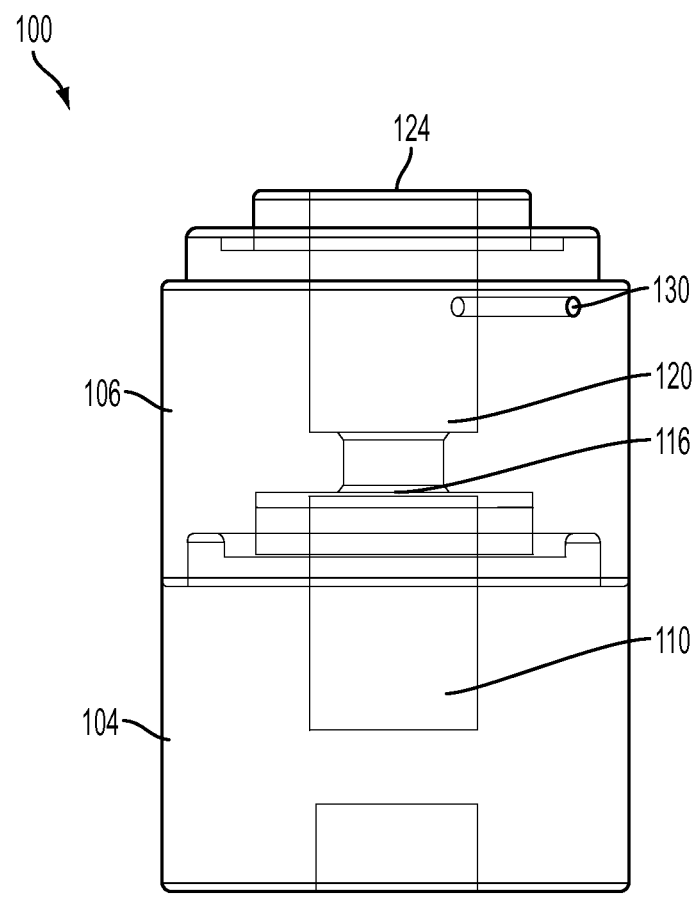
FIG. 7 is a partially transparent side view of another exemplary RH generator including a small lateral vent hole in the upper component.

FIG. 7 shows another exemplary RH generator 100 that includes a vent in upper chamber. The generator 100 includes a lower component 104 having a lower chamber 110, and an upper component 106 having an upper chamber 120. The chambers are separated by a first membrane 116. A second membrane 124 can be positioned over an upper opening of the upper chamber 120. The upper component 106 includes a small vent hole 130 that extends from the upper chamber 120 to the outside ambient environment. The vent hole 130 can extend laterally and/or radially through the body of the upper component 106, as illustrated, or can extend in any orientation through any part of the upper component to allow air to escape from the upper chamber out to the ambient environment. Any of the RH generator embodiments disclosed herein can optionally include such a vent hole.

A vent hole in the upper chamber of an RH generator can prevent over-pressurization from occurring in the upper chamber, which can occur if the upper chamber is completely sealed off (other than the pores in the membranes). Such over-pressurization could occur, for example, if the upper chamber is already charged (has a partially or completely filled salt solution) and then more liquid water is added to the lower chamber. The vent hole allows pressure build-up caused by over-charging the upper chamber to release automatically. Including the vent can consequently allow a user to refill the lower chamber when the upper chamber is already charged, rather than waiting until most of the water has dissipated from the system, in order to increase the effective capacity of the RH generator and allow it to remain charged for a longer period of time before needing to be re-filled with more water.

The vent hole can be small enough to minimize loss of desired equilibrium conditions in the upper chamber when in use, but large enough to allow for dissipation of excess air pressure build-up. For example, in some embodiments the vent hole has a diameter of from about 1/40 of an inch to about 1/32 of an inch. The vent hole can be positioned above the elevation of the salt positioned in the upper chamber so that the salt does not block the hole.

As shown in FIG. 7, the lower component 104 and the upper component 106 of the RH generator 100 can have differing geometries. For example, the lower component 104 shown in FIG. 7 does not include a lower opening or a plug to seal the lower chamber 110. Instead, the only outlet of the lower chamber 110 is its upper opening. To add water to the lower chamber 110, the lower component 104 is separated from the upper component 106 and water is poured into the upper opening. The two components can then be re-attached, such as via a compression fit or other engagement means. The membrane 116 can remain attached to the bottom of the upper component 106.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Numbers, values, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim at least all that comes within the scope of these claims.

The invention claimed is:

1. A relative humidity (RH) generator comprising:
    a lower component having a first chamber having an upper opening and being configured to contain liquid water and generate a first RH within the first chamber;
    an upper component including a second chamber having an upper opening and a lower opening, the upper component being coupled to the lower component to couple the upper opening of the first chamber to the lower opening of the second chamber, the second chamber being configured to contain salt and generate a second RH within the second chamber; wherein the second RH is predetermined based on the salt positioned in the second chamber; and a first membrane positioned between the first chamber and the second chamber to allow water vapor to pass between the first and second chambers through the first membrane;

wherein the upper component is adapted to be coupled to an RH probe with a second membrane separating the upper opening of the second chamber from the RH probe, such that the second membrane allows water vapor to pass between the second chamber and an RH sensor of the RH probe to thereby expose the RH sensor to the second RH;

wherein the RH generator is operable to distill ordinary tap water from the first chamber into to purified water vapor that passes through the first membrane; and wherein the second RH is lower than the first RH, and the RH generator is operable to distill water by causing water vapor from the first chamber to diffuse through the first membrane into the second chamber due to difference between the first RH and the second RH.

2. The RH generator of claim 1, wherein the RH generator is operable to generate and maintain the second RH at the predetermined value in the second chamber when the water in the first chamber is ordinary tap water.

3. The RH generator of claim 1, wherein the first membrane does not allow liquid water or the salt to pass through the first membrane.

4. The RH generator of claim 1, wherein the first membrane does not allow molecules substantially larger than water molecules to pass through the first membrane.

5. The RH generator of claim 1, wherein the second membrane is secured to the upper component and covers the upper opening of the second chamber.

6. The RH generator of claim 1, wherein the first membrane comprises polytetrafluoroethylene (PTFE).

7. The RH generator of claim 1, wherein the first chamber has a lower opening for adding water into the first chamber, and the RH generator includes a removable plug that seals the lower opening of the first chamber.

8. The RH generator of claim 1, wherein the lower component is identical to the upper component.

9. The RH generator of claim 1, wherein the lower component includes a first connection feature on its upper surface and the upper component includes a second connection feature on its lower surface, and the first and second connection features are configured to mate together to attach the lower component to the upper component.

10. The RH generator of claim 9, wherein the upper component includes a third connection feature on its upper surface for securing the RH generator to an RH probe.

11. The RH generator of claim 9, wherein the first and second connection features include corresponding concentric rims and recesses, wherein the rims insert into the recesses using to attach the lower component to the upper component.

12. The RH generator of claim 1, wherein the upper component includes an air vent hole that extends from the second chamber through the upper component to the external ambient environment.

13. The RH generator of claim 1, wherein the upper component comprises two or more separate chambers each configured to contain a different salt for generating different RH values, wherein the generator can be adjusted to two or more corresponding positions to put the first chamber in vapor communication with the each of the two or more separate chambers of the upper component, one at a time.

14. A relative humidity (RH) generator comprising:

a lower component having a first chamber having an upper opening and being configured to contain liquid water and generate a first RH within the first chamber;

an upper component including a second chamber having an upper opening and a lower opening, the upper component being coupled to the lower component to couple the upper opening of the first chamber to the lower opening of the second chamber, the second chamber being configured to contain salt and generate a second RH within the second chamber; wherein the second RH is predetermined based on the salt positioned in the second chamber; and a first membrane positioned between the first chamber and the second chamber to allow water vapor to pass between the first and second chambers through the first membrane;

wherein the upper component is adapted to be coupled to an RH probe with a second membrane separating the upper opening of the second chamber from the RH probe, such that the second membrane allows water vapor to pass between the second chamber and an RH sensor of the RH probe to thereby expose the RH sensor to the second RH; and wherein the first chamber has a lower opening for adding water into the first chamber, and the RH generator includes a removable plug that seals the lower opening of the first chamber.

15. The RH generator of claim 14, wherein the upper component comprises two or more separate chambers each configured to contain a different salt for generating different RH values, wherein the generator can be adjusted to two or more corresponding positions to put the first chamber in vapor communication with the each of the two or more separate chambers of the upper component, one at a time.

16. The RH generator of claim 14, wherein the RH generator is operable to generate and maintain the second RH at the predetermined value in the second chamber when the water in the first chamber is ordinary tap water.

17. The RH generator of claim 14, wherein the lower component includes a first connection feature on its upper surface and the upper component includes a second connection feature on its lower surface, and the first and second connection features are configured to mate together to attach the lower component to the upper component.

18. A relative humidity (RH) generator comprising:

a lower component having a first chamber having an upper opening and being configured to contain liquid water and generate a first RH within the first chamber;

an upper component including a second chamber having an upper opening and a lower opening, the upper component being coupled to the lower component to couple the upper opening of the first chamber to the lower opening of the second chamber, the second chamber being configured to contain salt and generate a second RH within the second chamber; wherein the second RH is predetermined based on the salt positioned in the second chamber; and a first membrane positioned between the first chamber and the second chamber to allow water vapor to pass between the first and second chambers through the first membrane;

wherein the upper component is adapted to be coupled to an RH probe with a second membrane separating the upper opening of the second chamber from the RH probe, such that the second membrane allows water vapor to pass between the second chamber and an RH sensor of the RH probe to thereby expose the RH sensor to the second RH; and wherein the upper component comprises two or more separate chambers each configured to contain a different salt for generating different RH values, wherein the generator can be adjusted to two or more corresponding positions to put the first chamber in vapor communication with the each of the two or more separate chambers of the upper component, one at a time.

19. The RH generator of claim 18, wherein the RH generator is operable to generate and maintain the second RH at the predetermined value in the second chamber when the water in the first chamber is ordinary tap water.

20. The RH generator of claim 18, wherein the lower component includes a first connection feature on its upper surface and the upper component includes a second connection feature on its lower surface, and the first and second connection features are configured to mate together to attach the lower component to the upper component.

\* \* \* \* \*